(12) United States Patent
Wada et al.

(10) Patent No.: US 8,267,516 B2
(45) Date of Patent: Sep. 18, 2012

(54) FUNDUS IMAGING APPARATUS AND METHOD THEREFOR

(75) Inventors: Manabu Wada, Kawasaki (JP); Motoya Takai, Negareyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 221 days.

(21) Appl. No.: 12/857,840

(22) Filed: Aug. 17, 2010

(65) Prior Publication Data

US 2011/0051089 A1    Mar. 3, 2011

(30) Foreign Application Priority Data

Aug. 27, 2009    (JP) ................................ 2009-196998

(51) Int. Cl.
*A61B 3/14*    (2006.01)
*A61B 3/00*    (2006.01)
(52) U.S. Cl. .................. 351/206; 351/208; 351/246
(58) Field of Classification Search .................. 351/206, 351/208, 246
See application file for complete search history.

(56) References Cited

U.S. PATENT DOCUMENTS 7,572,009 B2 *    8/2009    Suzuki ......................... 351/206

FOREIGN PATENT DOCUMENTS

JP    5-192299 A    8/1993

* cited by examiner

*Primary Examiner* — Jack Dinh
(74) *Attorney, Agent, or Firm* — Canon U.S.A., Inc., IP Division (57) ABSTRACT

A fundus image is displayed, which enables accurate positioning and focusing to be easily performed with respect to an eye to be examined even on a small display unit by selecting a display magnification. At a first display magnification, an opening portion "m" of a mask specifying a predetermined angle of field of the fundus is displayed with no part missed in both of horizontal and vertical directions of a display unit 15. At a second display magnification, the opening "m" of the mask is displayed with no part missed in the horizontal direction in the display area of the display unit 15 and with some part missed in the vertical direction. Thus, the second display magnification is used to observe an essential part when the fundus is accurately observed.

10 Claims, 9 Drawing Sheets

FUNDUS IMAGING APPARATUS AND METHOD THEREFOR

BACKGROUND OF THE INVENTION

1. Field of the Invention

The present invention relates to a fundus imaging apparatus that images a fundus of an eye to be examined and a method therefor.

2. Description of the Related Art

Conventional fundus cameras form on an image sensor an image reflected from a fundus of an eye to be examined and display on a display unit a fundus image, which is output from the image sensor, to be used for accurate positioning and focusing with respect to the eye to be examined.

The fundus image displayed on the display unit is electronically or optically provided with a mask that has an opening portion at a center thereof to specify a predetermined angle of field of the fundus image. A magnification is determined by a length of a shorter side (vertical direction) of a display unit or a display area having different vertical and horizontal lengths in a shorter side (vertical) direction and a length of the opening portion of the mask in the vertical direction of the display unit. The length of the shorter side (vertical direction) of the display unit is defined longer than that of the opening portion of the mask in the shorter side (vertical) direction of the display unit.

Further, to enlarge and observe a optic disk and a macular area of the fundus image, fundus cameras are known in which the fundus image is optically or electrically enlarged. Japanese Patent Application Laid-Open No. 5-192299 discusses a fundus camera capable of electronically enlarging and displaying an area specified at a specified display magnification by an operator when the operator observes the fundus image before shooting.

On the other hand, along with growing popularity of general-purpose digital cameras in recent years, the general-purpose digital camera is often used for the fundus camera. Further, in recent years, a method is discussed in which a general-purpose digital camera is mounted onto an optical system of the fundus camera, the image sensor provided in the general-purpose digital camera captures the fundus image, and then the captured fundus image is displayed on the display unit of the general-purpose digital camera.

The fundus camera, which is discussed in Japanese Patent Application Laid-Open No. 5-192299, enlarges the image immediately before shooting during the observation, and thus does not enlarge the image from when the observation is started until immediately before the image is captured. Therefore, when the fundus image that is not enlarged is displayed on a small display unit, the fundus image is displayed small, and therefore it is difficult for an operator to perform accurate positioning and focusing.

However, many general-purpose digital cameras include a small display unit. Since the fundus image is used for accurate positioning or focusing with respect to the eye to be examined, it is difficult to clearly observe the fundus image displayed on such a small display unit of the general-purpose digital camera.

SUMMARY OF THE INVENTION

The present invention is directed to a fundus imaging apparatus capable of displaying a fundus image at a display magnification, which is determined by a size of a display unit included in a fundus camera and a predetermined angle of field specified by an opening portion of a mask, and further capable of easily positioning and focusing with respect to an eye to be examined, even if the display unit is small.

According to an aspect of the present invention, a fundus imaging apparatus that captures a fundus image of an eye to be examined includes a display control unit configured to display on a display unit the fundus image combined with a mask having an opening portion, and a display magnification changing unit configured to change a display magnification of the fundus image. The display magnification changing unit can selectively change display magnifications between a first display magnification in which a length of the mask in a lateral direction (vertical direction, shorter side) of the display unit is shorter than a length of the display unit in the lateral direction, and a second display magnification in which the length of the mask in the lateral direction of the display unit is longer than the length of the display unit in the lateral direction and a length of the mask in a longitudinal direction (horizontal direction, longer side) of the display unit is within a length of the display unit in the longitudinal direction thereof.

According to another aspect of the present invention, a fundus imaging method for imaging a fundus of an eye to be examined includes displaying the fundus image combined with a mask having an opening portion at a first display magnification in which a length of the mask in a lateral direction of a display unit is within a length of the display unit in the lateral direction, and changing the first display magnification to a second display magnification in which the length of the mask in the lateral direction of the display unit is larger than the length of the display unit in the lateral direction.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
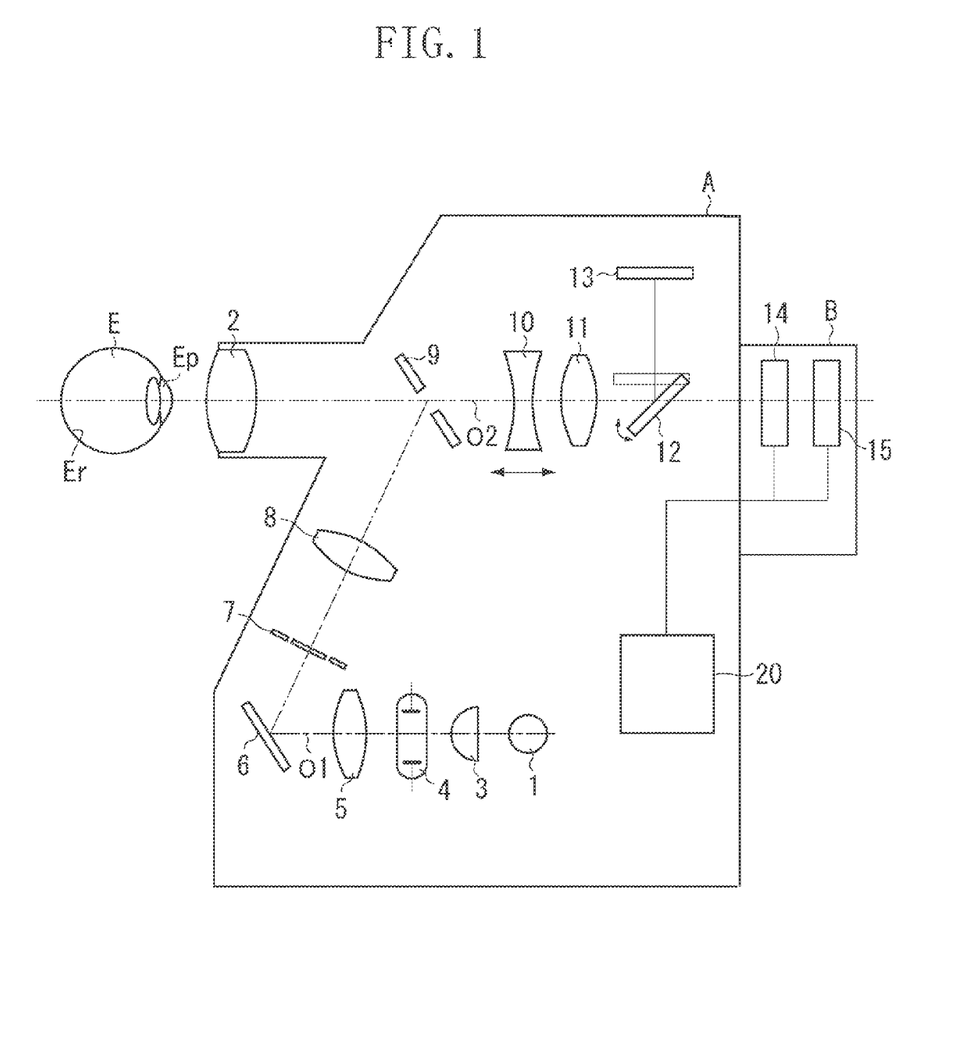
FIG. 1 illustrates a configuration of a fundus imaging apparatus according to a first exemplary embodiment.

FIG. 1 illustrates a configuration of a fundus imaging apparatus. A fundus camera "A" including an illumination optical system and a shooting optical system is detachably provided with a digital camera "B" that performs imaging and displaying. The camera "A" includes a fundus illumination optical system O1 extending from an observation light source 1 to an objective lens 2 facing an eye "E" to be examined.

On an optical path of the fundus illumination optical system O1, an observation light source 1 emitting infrared light, a condenser lens 3, a shooting light source 4 emitting visible light, a relay lens 5, a mirror 6, a diaphragm 7 having an opening in a ring shape, a relay lens 8, and a apertured-mirror 9 are arranged in sequence.

Further, on a optical path extending in a direction passing through a hole portion of the apertured-mirror 9, a focus lens 10, a shooting lens 11, a movable mirror 12, and a digital camera "B" are arranged to constitute a fundus shooting optical system O2.

A movable mirror 12 reflects the visible light and transmits the infrared light. When the image is observed, the movable mirror 12 is inserted into the light path, and when the image is captured, the movable mirror 12 is removed therefrom. On an optical path in a direction where light is reflected from the movable mirror 12, an internal fixation light 13 is disposed. In the internal fixation light 13, for example, fifteen light emitting diodes (LED) are disposed in a matrix pattern to lead a direction of a line of sight of an eye "E" to be examined.

The digital camera "B" includes an image sensor 14, such as a complementary metal oxide semiconductor (CMOS) sensor, and a display unit 15 that displays a captured image and has a shape having different vertical and horizontal lengths to each other. The fundus camera "A" includes a camera control unit 20, which is connected to the image sensor 14 and the display unit 15 in the digital camera "B".

Figure 2:
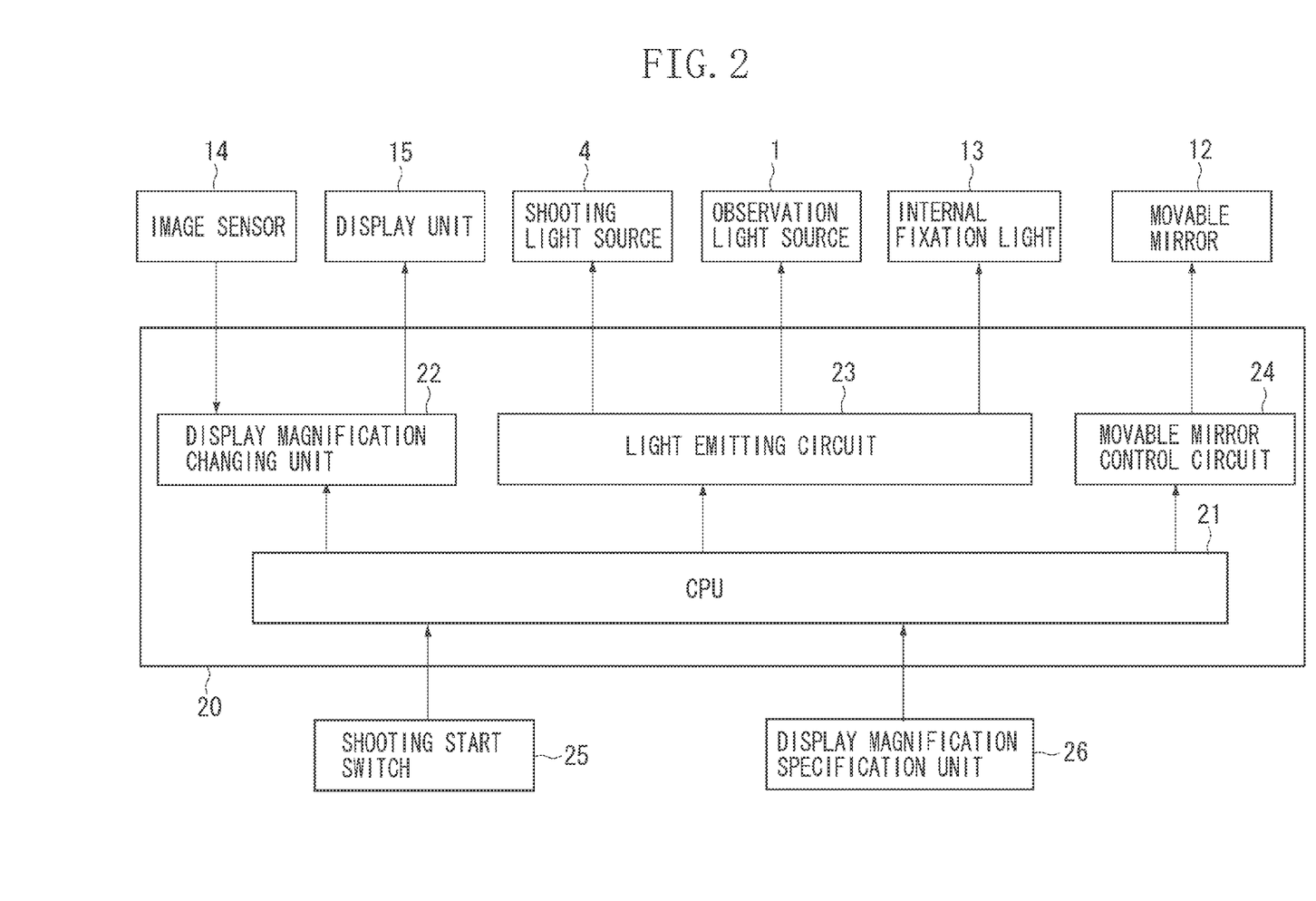
FIG. 2 is a block diagram illustrating a circuit configuration of a camera control unit.

FIG. 2 is a block diagram illustrating a circuit configuration of a camera control unit 20. The camera control unit 20 includes a central processing unit (CPU) 21, a display magnification changing unit 22, a light emitting circuit 23, and a movable mirror control circuit 24. An output from the CPU 21 is connected to the image sensor 14 and the display unit 15 in the digital camera "B" via the display magnification changing unit 22.

Further, via the light emitting circuit 23, an output from the CPU 21 is connected to the observation light source 1, the shooting light source 4, and the internal fixation light 13 in the fundus camera "A". Furthermore, via the movable mirror control circuit 24, an output from the CPU 21 is connected to the movable mirror 12 in the fundus camera "A". Moreover, outputs from a shooting start switch 25 and a display magnification specification unit 26 are connected to the CPU 21.

When an operator observes the fundus, the operator positions an eye "E" to be examined in front of the objective lens 2, and performs accurate positioning and focusing with respect to the eye "E" to be examined to capture the fundus image. When the observation light source 1 is lit by the light emitting circuit 23, infrared observation light is emitted through the fundus illumination optical system O1 from the observation light source 1 to the objective lens 2, and illuminates the fundus Er via a pupil Ep of the eye "E" to be examined.

The image of the fundus Er illuminated with the observation light passes through the fundus shooting optical system O2 including the objective lens 2, the apertured-mirror 9, and the movable mirror 12, and reaches the image sensor 14 in the digital camera "B". At this point, the movable mirror 12 has been already inserted into the light path, and the fundus image that is illuminated by the infrared light and obtained by the image sensor 14 is output to the display unit 15 by the display magnification changing unit 22.

The operator moves the fundus camera "A" by operating an operation lever up, down, right, or left while viewing the fundus image displayed on the display unit 15 to accurately perform positioning of the fundus camera "A" with respect to the eye "E" to be examined. Further, the operator operates a focus knob (not illustrated) to move a focus lens 10, so as to perform focusing.

After the operator checks that positioning and focusing have been performed correctly, the operator presses the shooting start switch 25 to capture the image of the fundus Er. When the operator operates the shooting start switch 25, the movable mirror control circuit 24 raises and removes the movable mirror 12 from the optical path, and then the light emitting circuit 23 causes the shooting light source 4 to emit light. Shooting light, which is the visible light, is emitted by the shooting light source 4 through the fundus illumination optical system O1 and illuminates the fundus Er.

As described above, the fundus image of the fundus Er illuminated by the shooting light source 4 passes through the objective lens 2 and the apertured-mirror 9 through the fundus shooting optical system O2, reaches the image sensor 14 in the digital camera "B", and is displayed on the display unit 15 as necessary. Further, the fundus image is recorded in a recording medium.

When the display unit 15 displays the fundus image captured by the image sensor 14, the display magnification changing unit 22 electronically combines the fundus image and a circle mask that has an opening at a center thereof and specifies a predetermined angle of field of the fundus Er. Subsequently, the display magnification changing unit 22 performs enlarging processing on the opening portion of the mask and the fundus image at a plurality of magnifications (first and second display magnifications) provided by the display magnification changing unit 22, and displays the enlarged mask and fundus image.

Figure 3A:
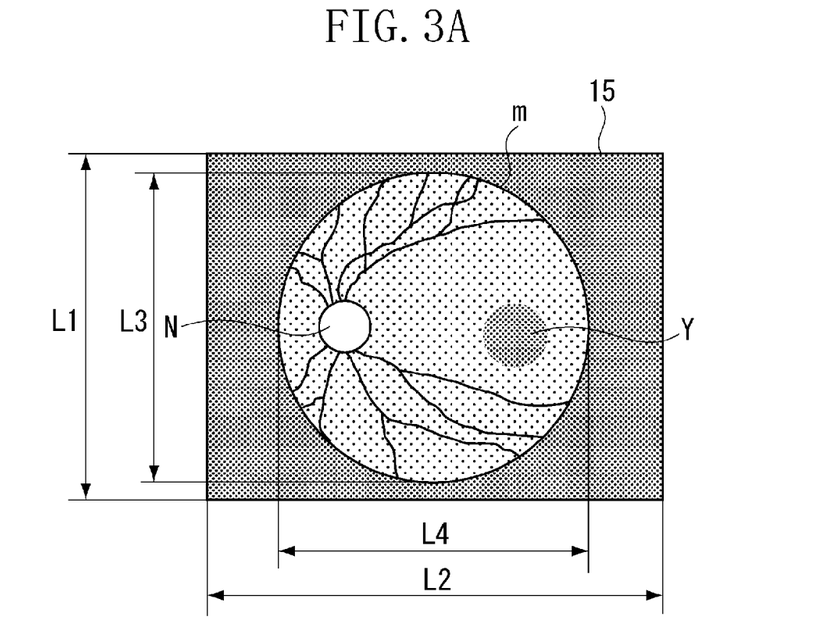
FIGS. 3A and 3B each illustrate a fundus image displayed on a display unit.
Figure 3B:
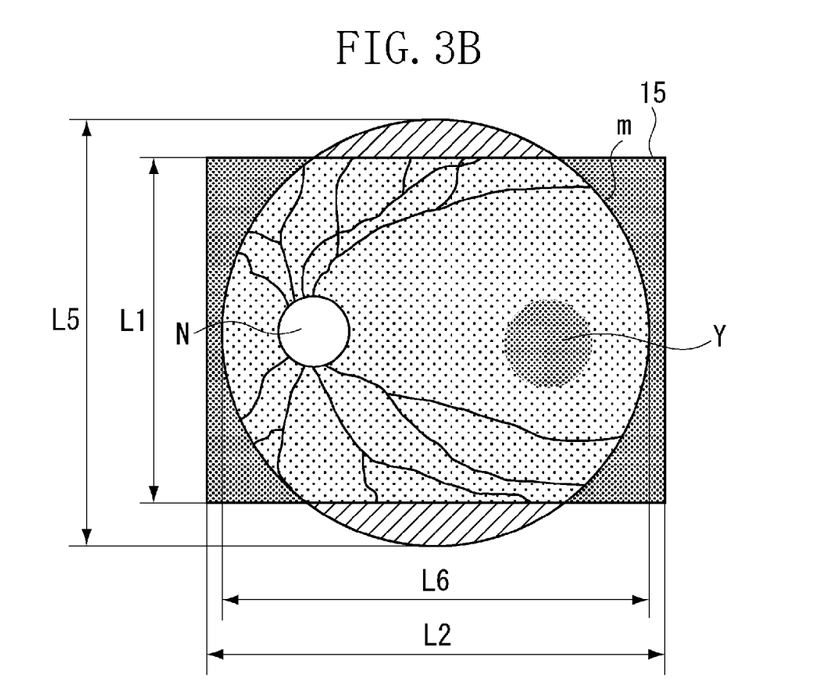

FIG. 3A illustrates the fundus image displayed with the first display magnification in the display area of the display unit 15 by the display magnification changing unit 22. FIG. 3B is the fundus image displayed at the second display magnification.

FIGS. 3A and 3B each include an opening portion "m" of the electronic masks applied to specify the predetermined angle of field of the fundus Er. A length L1 is a length of the display area of the display unit 15 in a lateral direction (vertical direction, shorter side), a length L2 is a length in a longitudinal direction (horizontal direction, longer side) thereof, a length L3 is a length of the opening portion "m" of the mask in an L1 direction at the first display magnification, and a length L4 is a length of the opening portion "m" of the mask in an L2 direction of L2 at the first display magnification. Further, a length L5 is a length of the opening portion "m" of the mask in the L1 direction at the second display magnification, and a length L6 is a length of the opening portion "m" of the mask in the L2 direction at the second display magnification.

The first display magnification is determined by the lengths L1 and L3. More specifically, this magnification satisfies, when L1 is almost the same as L3, $L1 \geqq L3$. At this magnification, the opening portion "m" of the mask specifying the predetermined angle of field of the fundus Er can be displayed with no part missed in both of the longitudinal and lateral directions of the display area of the display unit 15. The first display magnification is described in "BACKGROUND OF INVENTION".

The second display magnification is determined by the lengths L1 and L5, and the lengths L2 and L6. More specifically, this magnification satisfies that, when L2 is almost the same as L6, L2≧L6, and L1≦L5. The opening portion "m" of the mask at the second display magnification is larger than that at the first display magnification. At the second magnification, the opening portion "m" of the mask specifying the predetermined angle of field of the fundus Er can be displayed with no part missed in the longitudinal direction, and with some part missed in the lateral direction.

At the second display magnification, the operator can easily perform positioning and focusing even on the small display unit 15. This is for the following reasons. For example, a posterior pole, where a macular portion "Y" and an optic disk "N" have an even positional relationship, is captured as a main part as illustrated in FIG. 3. In general, the operator performs positioning and focusing between the fundus Er and the fundus camera "A" when observing, while viewing positional relationships among the macular portion "Y", the optic disk "N", a main artery, and a vein of the fundus image.

When the image is displayed at the second display magnification, for example, when an aspect ratio of general four to three or sixteen to nine of the display unit 15 is assumed, a part of the fundus image that is missing and thus not displayed is indicated as a shaded part as illustrated in FIG. 3B. The missing part does not include the macular portion "Y", the optic disk "N", the main artery, and the vein. Therefore, the missing part does not hinder positioning and focusing even if the missing part is not displayed.

As described above, at the second display magnification, the part that does not hinder positioning nor focusing are not displayed, but the part necessary for positioning and focusing is enlarged and displayed. Thus, positioning and focusing can be easily performed even on the small display unit 15.

According to the present exemplary embodiment, although the second display magnification can be adopted, when the observation can be sufficiently performed at the first display magnification, the first display magnification can be selected using the display magnification specification unit 26. In other words, according to a usage of the operator, the first and second display magnifications can be selectively changed, thereby enabling a convenient use.

For a more convenient use, when the fundus image is displayed on the display unit 15, the display magnification changing unit 22 may electronically combines the fundus image and the mask having the opening at the center thereof specifying the predetermined angle of field of the fundus Er, so that the image can be displayed at the first display magnification for any specification by the display magnification specification unit 26.

Since the fundus image displayed on the display unit 15 is to be used for checking whether the whole image of the predetermined angle of field specified by the opening portion "m" of the mask is captured, the image needs to be displayed at the first display magnification. If the fundus image is displayed at the second display magnification, at which the whole image of the predetermined angle of field cannot be displayed, a capturing mistake is difficult to be checked.

According to the present exemplary embodiment, the image sensor 14 and the display unit 15 are included in the digital camera "B", which is detachable with respect to the fundus camera "A", but may be included in the fundus camera "A" not the digital camera "B". When the image sensor 14 and the display unit 15 are included in the digital camera "B", the fundus camera "A" that displays the fundus image and performs easy positioning and focusing can be obtained. That is because, in recent years, the image sensor 14 of the digital camera "B" has highly improved resolution, and the display unit 15 displays highly fine images. Thus, if the digital camera "B" can be provided detachably, the display unit 15 can be easily exchanged depending on the image sensor 14.

The present exemplary embodiment uses the electronic mask as an example, however, an optical mask may be used instead of the electronic mask. Further, according to the present exemplary embodiment, the display magnification changing unit 22 is included in the fundus camera "A", however, may be included in the digital camera "B" or a control apparatus such as a personal computer, which is externally connected to the fundus camera "A".

The present exemplary embodiment describes the observation light source 1 as a light source emitting the infrared light, however, may be the light source emitting the visible light. Note that, when the observation light source 1 emits the visible light, the movable mirror 12 must be removed from the optical path when the observation is performed.

Figure 4:
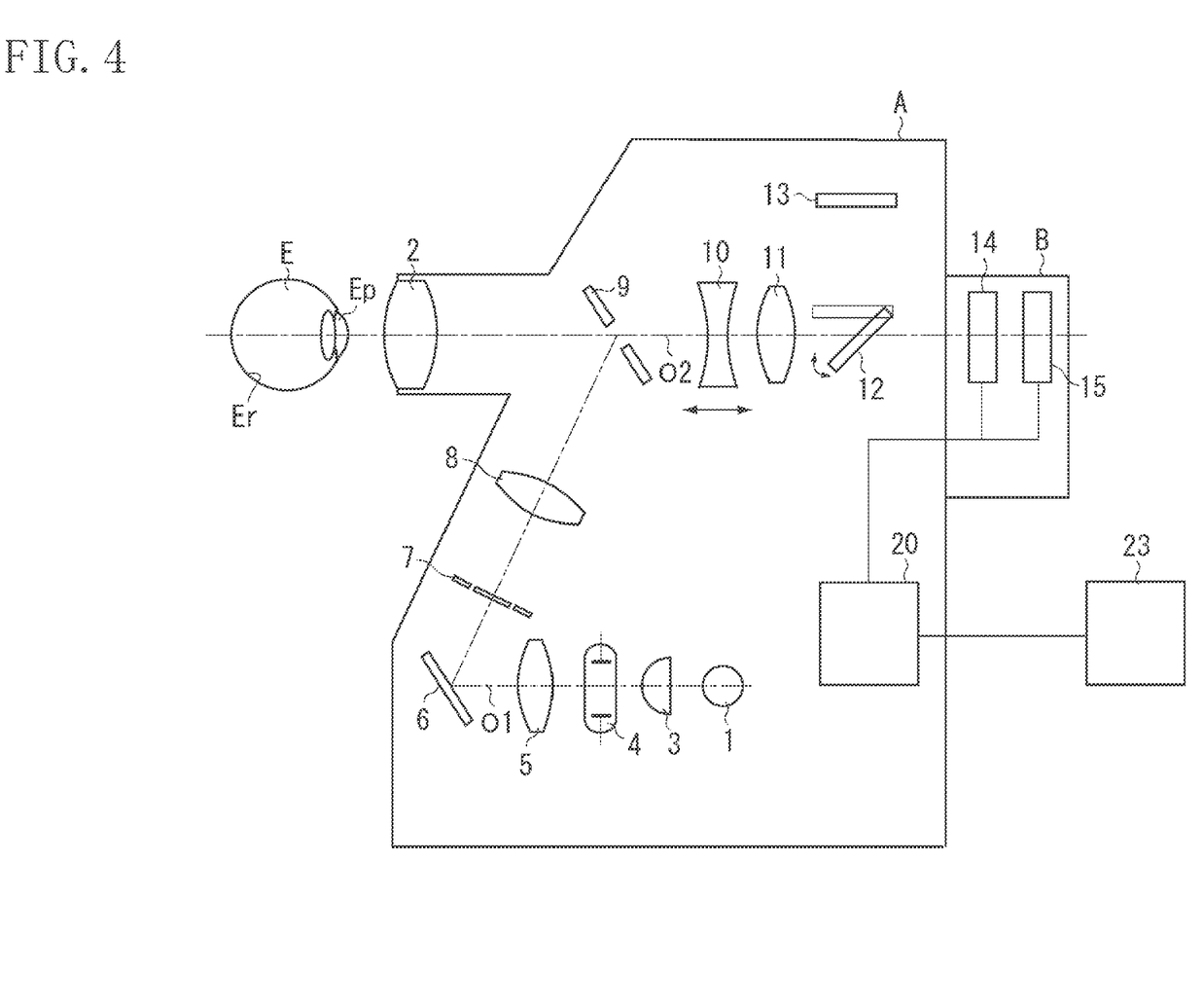
FIG. 4 illustrates a configuration of a fundus imaging apparatus according to a second exemplary embodiment.

FIG. 4 illustrates a configuration of a second exemplary embodiment. The same reference numerals are given to the same components as those illustrated in FIG. 1. In addition to members illustrated in FIG. 1, in FIG. 4, an external display unit 31 having a large display unit is externally connected to the camera control unit 20. Outputs from the display magnification changing unit 22 are connected to the external display unit 31.

Figure 5:
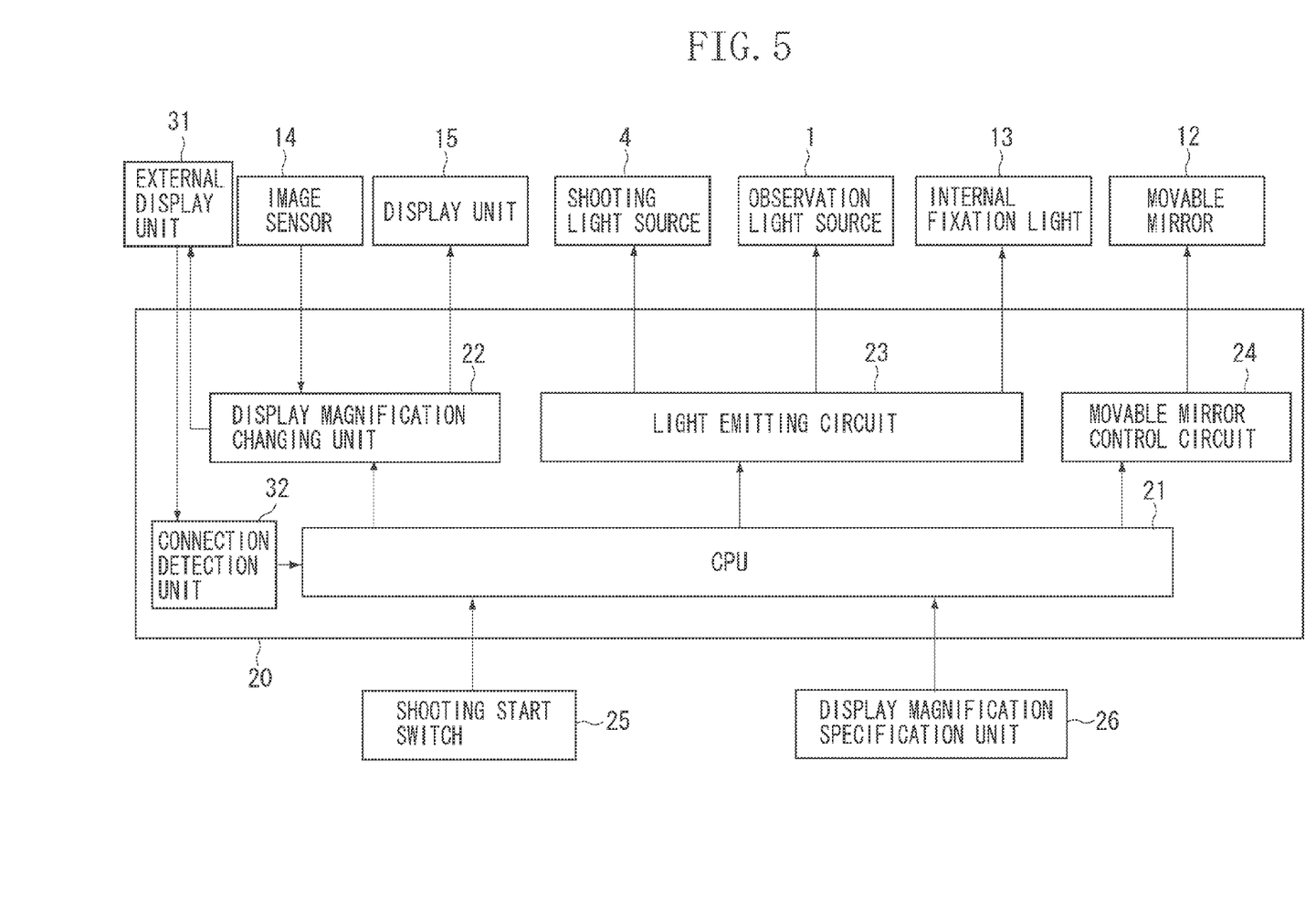
FIG. 5 is a block diagram illustrating a circuit configuration of a camera control unit.

FIG. 5 is a block diagram illustrating a circuit configuration of the camera control unit 20. The external display unit 31 is connected to the CPU 21 via a connection detection unit 32 in the camera control unit 20.

When the connection detection unit 32 detects that the external display unit 31 is connected to the fundus camera "A", the connection detection unit 32 notifies the CPU 21, which subsequently notifies the display magnification changing unit 22 that the external display unit 31 is connected to the fundus camera "A". The display magnification changing unit 22 electronically combines the fundus image captured by the image sensor 14 with the light emitted by the observation light source 1 with the mask that has the opening at the center thereof and specifies the predetermined angle of field of the fundus Er. The combined fundus image and mask is displayed on the external display unit 31 at the first display magnification.

The external display unit 31 is externally connected to the fundus camera "A", so that the fundus image can be observed on the display unit, which is larger than the display unit 15 of the digital camera "B". The first display magnification is used to observe the fundus image from all angles of field, when the fundus image is displayed on the external display unit 31 having the larger display unit, the operator can easily perform positioning and focusing with respect to the eye "E" to be examined. On the other hand, the second display magnification is used to easily observe essential parts of the fundus image even on the small display unit. Thus, when the large display unit is used, the second display magnification is not necessarily to be used.

Further, even if the display magnification specification unit 26 specifies the second display magnification, when the external display unit 31 is connected to the fundus camera "A", the first display magnification may be automatically set to perform display, for a convenient use.

In a third exemplary embodiment, configurations of the fundus camera "A" and the camera control unit 20 are similar to those in the first exemplary embodiment. Further, an observation and shooting procedures performed by the fundus camera "A" are similar to those in the first exemplary embodiment.

When the observation is performed, the light emitting circuit 23 of the camera control unit 20 emits any of LEDs in the matrix of the internal fixation light 13. The display magnification changing unit 22 electronically combines the fundus image captured by the image sensor 14 with the light emitted by the observation light source 1 and the mask that has the opening at the center thereof and specifies the predetermined angle of field of the fundus Er. The display magnification changing unit 22, then, performs enlarging processing at either of the first and second magnifications to display the fundus image on the display unit 15. Simultaneously, the display magnification changing unit 22 receives a setting position of the internal fixation light 13 by the light emitting circuit 23, combines the fundus image and characters indicating the setting positions, and displays the combined fundus image and characters.

Figure 6A:
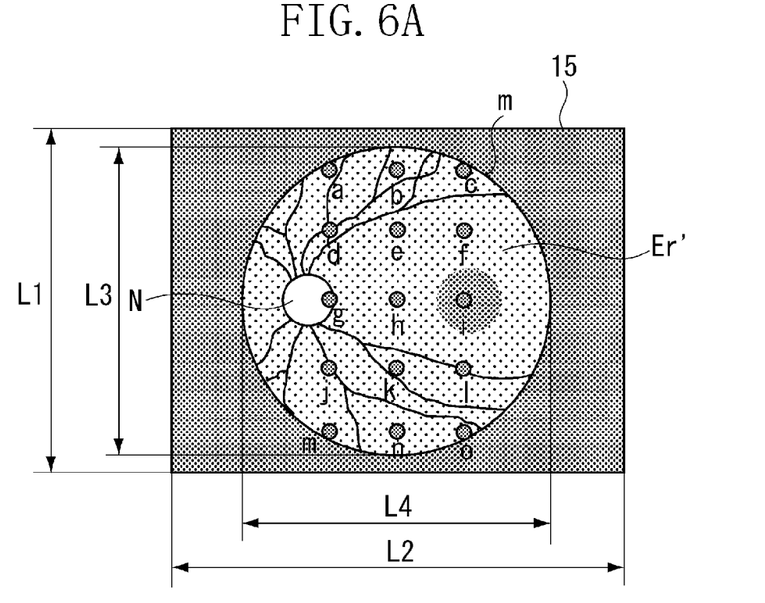
FIGS. 6A and 6B each illustrate a fundus image and a setting position of an internal fixation light displayed on a display unit, according to a third exemplary embodiment.
Figure 6B:
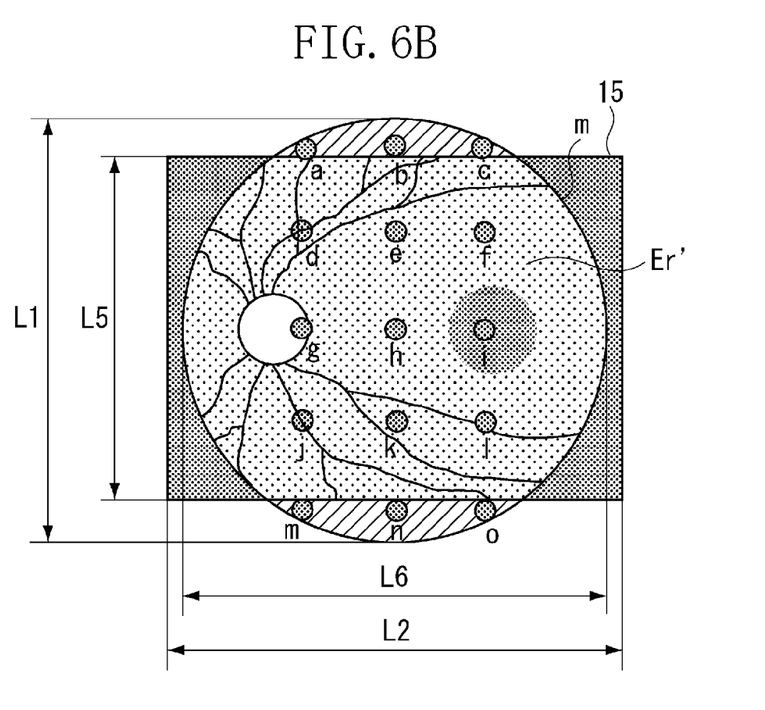

FIGS. 6A and 6B illustrate the fundus images Er' and the characters "a", "b", "c", "d", "e", "f", "g", "h", "i", "j", "k", "l", "m", "n", and "o" indicating the setting positions of the internal fixation light 13 displayed by the display magnification changing unit 22 in the display area of the display unit 15. FIG. 6A illustrates a case where the fundus image and the characters are displayed at the first display magnification, and illustrates all setting positions of the fifteen LED included in the internal fixation light 13 for descriptions. However, since the light is fixed, the setting position of one of the fifteen LED included in the internal fixation light 13 is actually combined with the fundus image and then displayed.

On the other hand, FIG. 6B illustrates a case where the fundus image and the characters are displayed at the second display magnification. Since the second display magnification enlarges the fundus image larger than the first display magnification, the characters "a", "b", "c", "m", "n", and "o" of the setting positions of the internal fixation light 13 in shaded parts are located outside the display area.

When the fundus image Er' is displayed on the display unit 15 at the second display magnification and the setting position of the internal fixation light 13 is moved to any one of the characters "a", "b", "c", "m", "n", and "o", the display magnification changing unit 22 changes the display magnification from the second display magnification to the first display magnification. With this arrangement, even if the internal fixation light 13 is moved to the outside of the display area of the display unit 15, the second display magnification is automatically switched to the first display magnification.

On the other hand, when the setting position of the internal fixation light 13 is moved from any one of the characters "a", "b", "c", "m", "n", and "o" to any one of the characters "d", "e", "f", "g", "h", "i", "j", "k", and "l", the first display magnification may be automatically switched to the second display magnification.

Figure 7:
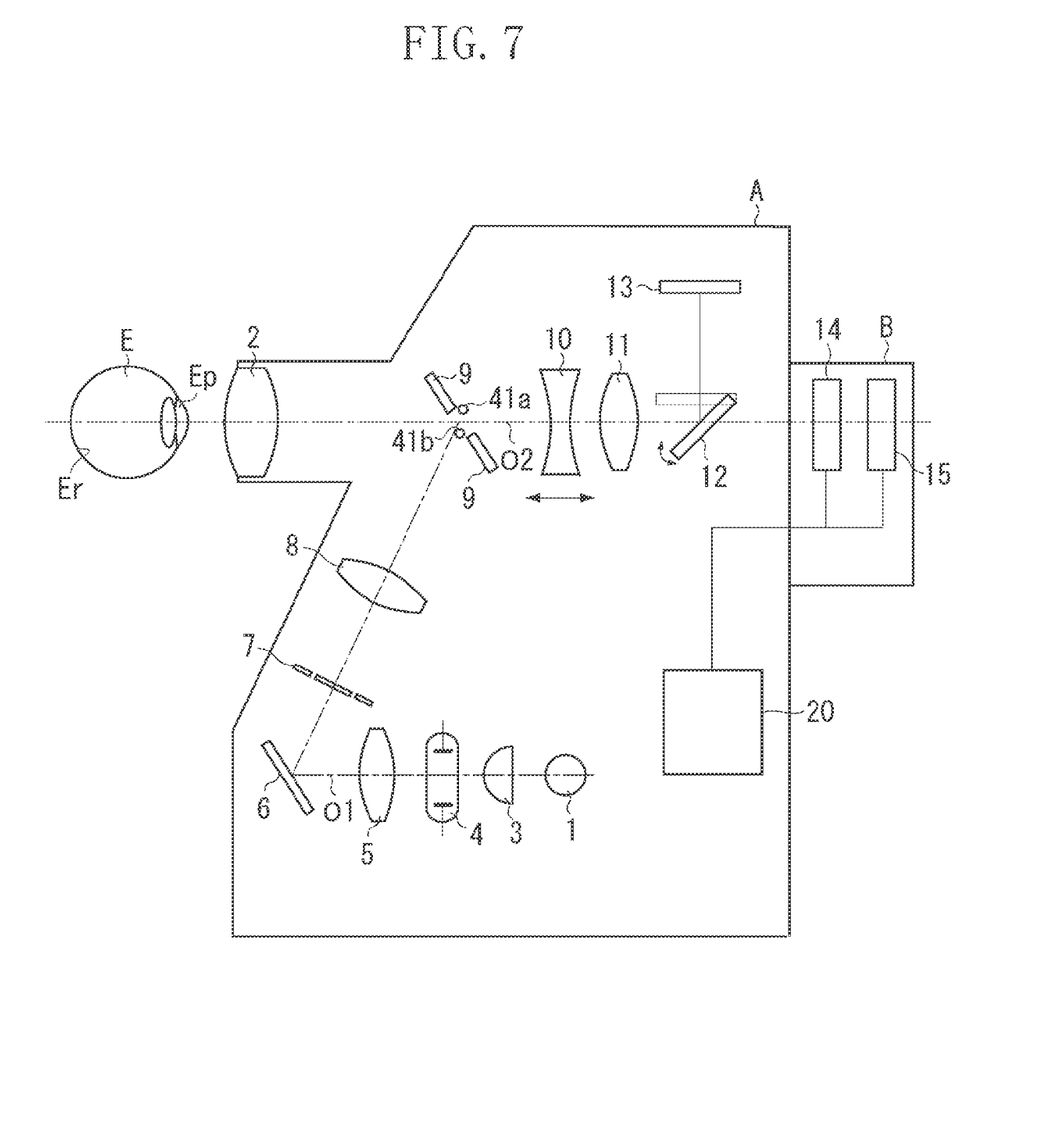
FIG. 7 illustrates a configuration of a fundus imaging apparatus according to a fourth exemplary embodiment.

FIG. 7 illustrates a configuration of a fourth exemplary embodiment. The same reference numerals are given to the similar components to those illustrated in FIG. 1. Alignment index light sources 41a and 41b that project an alignment indexes onto the eye "E" to be examined are disposed at both end portions in a hole of the apertured-mirror 9. The alignment index light sources 41a and 41b emit light having a wavelength of the infrared light, when the observation is performed.

Figure 8:
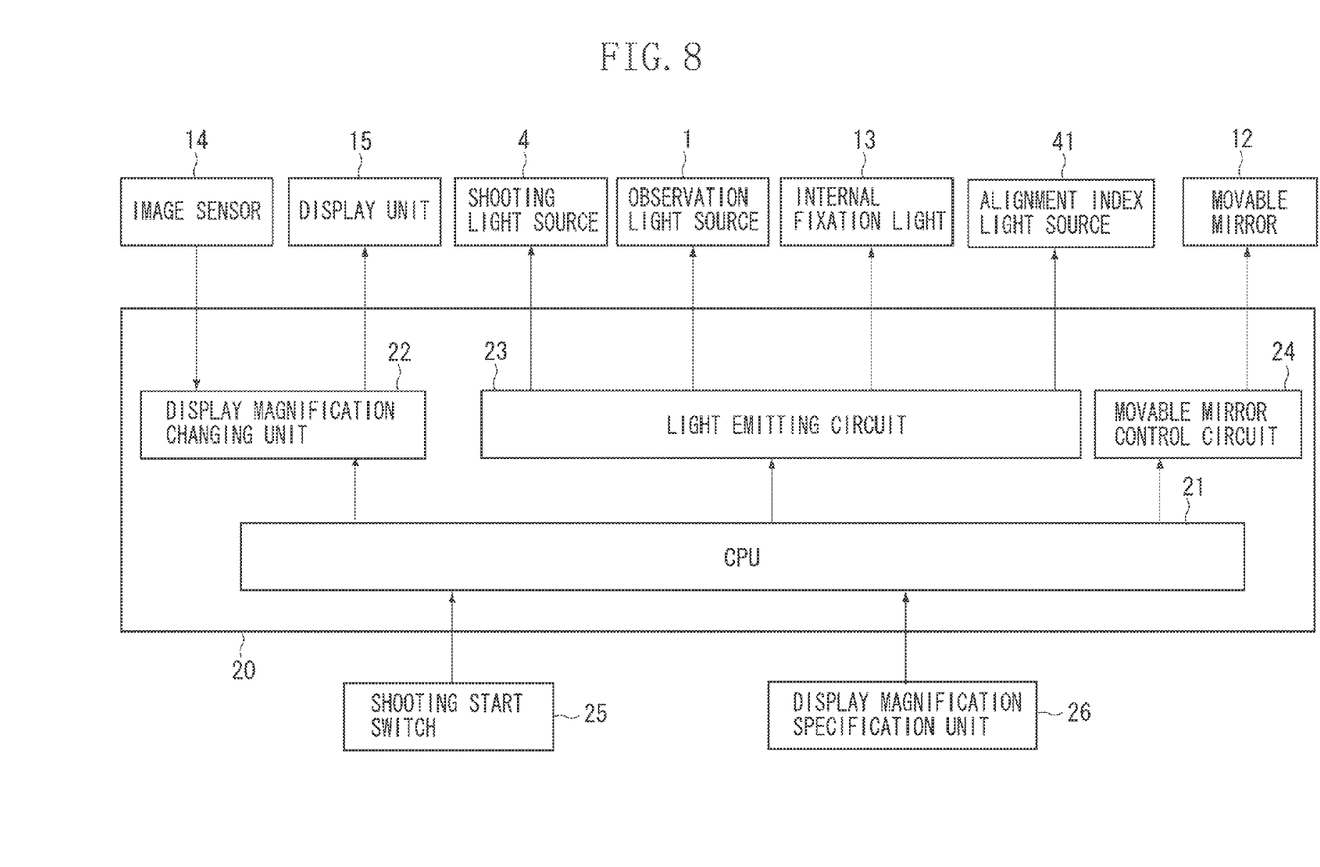
FIG. 8 is a block diagram illustrating a circuit configuration of a camera control unit.

FIG. 8 is a block diagram illustrating a circuit configuration of the camera control unit 20. In addition to the configuration illustrated in FIG. 2, the light emitting circuit 23 of the camera control unit 20 controls the alignment index light sources 41a and 41b to emit the light.

The observation and shooting procedures performed by the fundus camera "A" are similar to those in the first exemplary embodiment. The fundus image illuminated by the observation light source 1 when being observed and reflection images Pa and Pb of the alignment indexes illuminated by the respective alignment index light sources 41a and 41b are captured by the image sensor 14. Both of the fundus image and the reflection images Pa and Pb are displayed on the display unit 15.

Figure 9A:
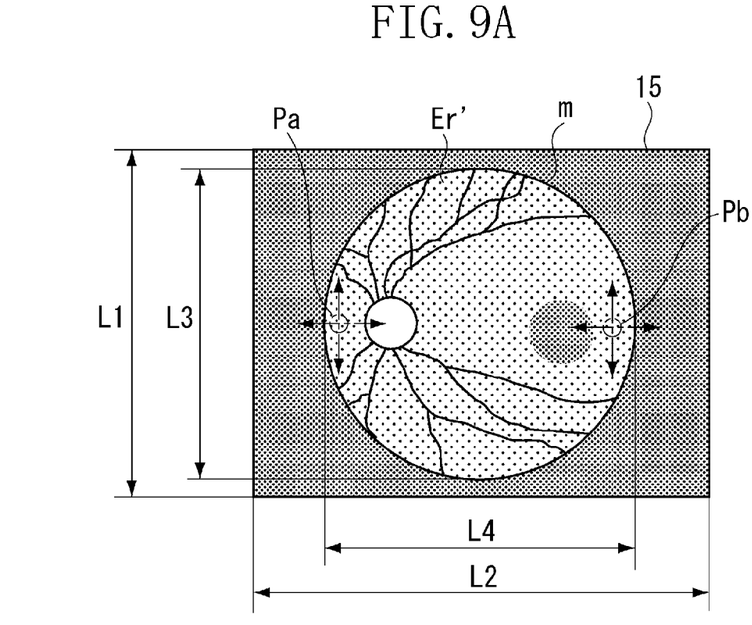
FIGS. 9A and 9B each illustrate a fundus image and a reflection image of an alignment index light source displayed on a display unit.
Figure 9B:
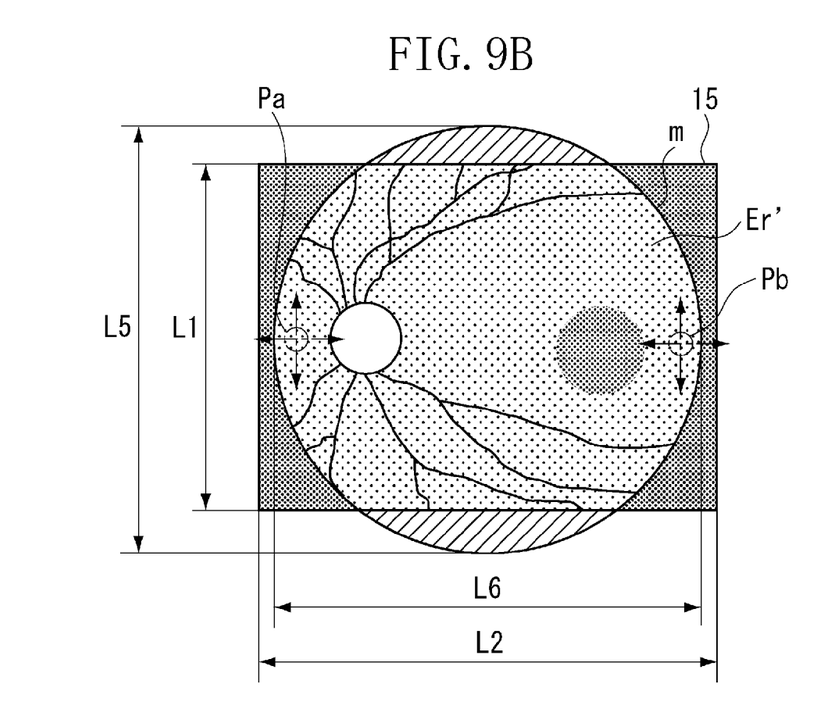

FIGS. 9A and 9B illustrate the fundus images Er' captured from the fundus Er and the reflection images Pa and Pb of the alignment indexes displayed on the display unit 15 when the observation is performed. FIG. 9A illustrates a case where the first display magnification is used. FIG. 9B illustrates a case where the second display magnification is used. The two reflection images Pa and Pb of the respective two alignment index light sources 41a and 41b are disposed at positions on one straight line in the horizontal direction of the display unit 15, when being displayed on the display unit 15.

The operator performs positioning including an operation distance between the eye "E" to be examined and the fundus camera "A", while observing the reflection images Pa and Pb of the alignment indexes and the fundus image Er'. By operating the operation lever, the two reflection images Pa and Pb of the respective alignment index light sources 41a and 41b move simultaneously up, down, right, or left in arrow directions. Thus, the operation distance can be adjusted by moving the reflection images Pa and Pb to certain predetermined positions in the fundus image Er'.

As described above, at the second magnification, the opening portion "m" of the mask specifying the predetermined angle of field of the fundus Er are displayed with no part missed in the horizontal direction in the display area, and with some parts missed in the vertical direction of the display area of the display unit 15. Therefore, the fundus image enabling easy positioning with respect to the eye "E" to be examined can be obtained by disposing and projecting the reflection images Pa and Pb, in such a manner that the reflection images Pa and Pb can be positioned on the straight line in the horizontal direction of the display unit 15.

On the other hand, if the reflection images Pa and Pb are positioned on the straight line in the vertical direction, since the fundus image is displayed with some part missed in the vertical direction at the second display magnification, positioning between the eye "E" to be examined and the fundus camera "A" becomes difficult.

According to the fourth exemplary embodiment, the two alignment index light sources 41a and 41b are projected. However, a similar effect can be obtained by using one alignment index light source, which can be observed as two indexes during positioning. In this case, the two indexes are operated to form one image by positioning.

The alignment index light sources 41a and 41b may emit the visible light. In this case, when the observation is performed, the movable mirror 12 reflecting the visible light needs to be removed from the optical path.

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-196998 filed Aug. 27, 2009, which is hereby incorporated by reference herein in its entirety.

What is claimed is:

1. A fundus imaging apparatus that captures a fundus image of an eye to be examined, the fundus imaging apparatus comprising:
a display control unit configured to display on a display unit the fundus image combined with a mask having an opening portion; and
a display magnification changing unit configured to change a display magnification of the fundus image,
wherein the display magnification changing unit can selectively change display magnifications between a first display magnification in which a length of the mask in a vertical direction of the display unit is shorter than a length of the display unit in the vertical direction, and a second display magnification in which the length of the mask in the vertical direction of the display unit is longer than the length of the display unit in the vertical direction and a length of the mask in a horizontal direction of the display unit is within a length of the display unit in the horizontal direction.

2. The fundus imaging apparatus according to claim 1, wherein the display unit has a shape having different vertical and horizontal lengths to display the fundus image.

3. The fundus imaging apparatus according to claim 1, further comprising an image sensor configured to capture light reflected from the fundus of the eye to be examined illuminated with illumination light from an illumination optical system as the fundus image via a shooting optical system,
wherein the image sensor and the display unit are detachable with respect to the shooting optical system.

4. The fundus imaging apparatus according to claim 1, further comprising:
an external display unit including a display area larger than a display area of the display unit to display the fundus image; and
a connection detection unit configured to detect whether the external display unit is connected,
wherein the display magnification changing unit displays the fundus image on the external display unit at the first display magnification based on an output of the connection detection unit, when the external display unit is connected.

5. The fundus imaging apparatus according to claim 1, further comprising:
an inner fixation light configured to lead a line of sight of the eye to be examined,
wherein settings of the inner fixation light are superimposed on the fundus image to be displayed, and
wherein, when display of the inner fixation light is moved to a position over a display area of the fundus image displayed at the second display magnification, the display magnification changing unit displays the fundus image at the first display magnification.

6. The fundus imaging apparatus according to claim 1, further comprising a projection unit configured to project a plurality of alignment indexes to perform alignment,
wherein the plurality of alignment indexes projected by the projection unit are arranged in the horizontal direction of the display unit.

7. A fundus imaging method for imaging a fundus of an eye to be examined comprising:
displaying the fundus image combined with a mask having an opening portion at a first display magnification in which a length of the mask in a vertical direction of a display unit is within a length of the display unit in the vertical direction; and
changing the first display magnification to a second display magnification in which the length of the mask in the vertical direction of the display unit is larger than the length of the display unit in the vertical direction and a length of the mask in a horizontal direction of the display unit is within a length of the display unit in the horizontal direction thereof.

8. A program for executing the fundus imaging method according to claim 7 by a computer.

9. A fundus imaging apparatus comprising:
an acquisition unit configured to acquire a fundus image combined with a mask having an opening portion; and
a display control unit configured to control a display unit to display the fundus image with a magnification in which a length of the mask in a vertical direction of the display unit is longer than a length of a display unit in the vertical direction, and the length of the mask in the horizontal direction of the display unit is shorter than the length of the display unit in the horizontal direction.

10. The fundus imaging apparatus comprising,
an acquisition unit configured to acquire a fundus image combined with a mask having an opening portion; and
a display control unit configured to control a display unit to display the fundus image with a magnification in which the length of the mask in the horizontal direction of the display unit is approximately equal to the length of the display unit in the horizontal direction.

* * * * *